United States Patent [19]

Bevilacqua et al.

[11] Patent Number: 5,081,034
[45] Date of Patent: Jan. 14, 1992

[54] CLONED GENES WHICH ENCODE ELAM-1

[75] Inventors: Michael P. Bevilacqua, Holbrook; Michael A. Gimbrone, Jamaica Plain; Brian Seed, Boston, all of Mass.; Siegfried Stengelin, Hofheim, Fed. Rep. of Germany

[73] Assignee: Brigham & Women's Hospital, Boston, Mass.

[21] Appl. No.: 270,873

[22] Filed: Nov. 14, 1988

[51] Int. Cl.$^5$ .................. C07H 15/10; C12N 5/10; C12N 1/13; C12N 15/12

[52] U.S. Cl. .................. 435/252.33; 435/240.2; 435/320.1; 435/252.3; 536/27; 935/9; 935/70; 935/71; 935/72

[58] Field of Search .................. 435/69.1, 91, 252.3, 435/320; 536/27

[56] References Cited

U.S. PATENT DOCUMENTS 4,727,028  2/1988  Santerre et al. ............. 435/240.2
4,740,470  4/1988  Cohen et al. ............. 435/172.3

OTHER PUBLICATIONS

Hunkapiller et al., 1983, Methods in Enzymology 91, 399-413.
Berger et al. (eds.), 1987, Methods in Enzymology 152, 307-451, 522-562, and 684-704.
Klein, J. 1982, in: *Immunology, The Science of Self-Nonself Discrimination*, John Wiley and Sons, New York, pp. 94, 310, 311, and 316.
Seed et al., *Proc. Natl. Acad. Sci. USA* 84:3365-3369 (1987).
Aruffo et al., *Proc. Natl. Acad. Sci. USA* 84:8573-8577 (1987).
Pober et al., *J. Immunol.* 136:1680-1687 (1986).
Bevilacqua et al., 4th Intl. Symp. on the Biol. Vasc. Endothel. Disease, p. 13, (1986 Aug.).
Pober et al., *J. Immunol.* 137:1893-1896 (1986).
Cotran et al., *J. Exp. Med.* 164:661-666 (1986).
Bevilacqua et al., *Feder. Proc.* 46:405 (1987).
Gimbrone et al., *Thromb. Hemostas.* 58:325 (1987).
Bevilacqua et al., in: Movat (ed.) *Leukocyte Emigration and Its Sequelae*, Satell, Symp., 6th Int'l. Congr. Immunol., Krager, Basel, 1987, pp. 79-93.
Bevilacqua et al., *Sem. Thromb. Hemostas.* 13:425-433 (1987).
Bevilacqua et al., *Proc. Natl. Acad. Sci. USA* 84:9238-9242 (1987).
Harlan, *Blood* 65:513-525 (1985).
Bevilacqua et al., *J. Clin. Invest.* 76:2003-2011 (1985).
Bevilacqua et al., *Am. J. Pathol.* 121:393-403 (1985).
Gamble et al., *Proc. Natl. Acad. Sci. USA* 82:8667-8671 (1985).
Dunn et al., in: M. Kluger, ed., *The Physiologic, Metabolic, and Immunologic Actions of Interleukin-1*, Alan R. Liss, Inc., 1985, pp. 45-54.
Simpson et al., *FASEB J.* 2(5):A1237 (1988).
Rothlein et al., *J. Immunol* 137:1270-1274 (1986).
Dustin et al., *J. Immunol.* 137:245-254 (1986).
Mentzer et al., *J. Cell Physiol.* 126:285-290 (1986).
Bevilacqua et al., *Science* 243:1160-1165 (1989).

(List continued on next page.)

Primary Examiner—Jacqueline Stone
Assistant Examiner—Christopher S. F. Low
Attorney, Agent, or Firm—Sterne, Kessler, Goldstein & Fox

[57] ABSTRACT

The invention relates to cloned genes, or degenerate variants thereof, which encode endothelial-leukocyte adhesion molecule-1 (ELAM-1), or fragments thereof. Such fragments may be leukocyte or complement-binding. The invention also relates to cloned genes encoding fusion proteins comprising ELAM. The invention also relates to vectors containing the cloned genes of the invention, hosts transformed with the vectors, and the protein products expressed therefrom. The invention also relates to pharmaceutical compositions comprising the expressed proteins. The invention also relates to methods for the treatment of inflammation, post reperfusion injury, bacterial infections, vasculitis, leukemia, and methods of inhibiting metastatic spread of tumor cells by administering the pharmaceutical compositions of the invention.

3 Claims, 2 Drawing Sheets

OTHER PUBLICATIONS

Jalkanen et al., *J. Cell Biol.* 105:983-990 (1987).
Jalkanen et al., *J. Immunol.* 141:1615-1623 (1988).
Stamenkovic et al., *Cell* 56:1057-1062 (1989).
International Search Report for Applicants' co-pending PCT Application No. PCT/US89/05073.
Polte, T. et al., *Nucl. Acids Res.* 18: 1903 (1989).
Hession, C. et al., *Proc. Natl. Acad. Sci. (USA)* 87: 1673-1677 (1990).
Collins, T. et al., *J. Biol. Chem.* 266: 2466-2473 (1991).
Bevilacqua, M. B. et al., *Science* 243: 1160-1165 (1989).
Walz, G. et al., *Science* 250: 1132-1135 (1990).
Phillips, M. et al., *Science* 250: 1130-1132 (1990).

CLONED GENES WHICH ENCODE ELAM-1

STATEMENT AS TO RIGHTS TO INVENTIONS MADE UNDER FEDERALLY SPONSORED RESEARCH AND DEVELOPMENT

Part of the work leading to this invention utilized U.S. Government funds. The U.S. Government has certain rights in this invention.

FIELD OF THE INVENTION

The invention is in the field of recombinant genetics.

BACKGROUND OF THE INVENTION

Focal adhesion of leukocytes to the endothelial lining of blood vessels is a characteristic step in inflammation and in certain vascular disease processes. Although it has long been suspected that alterations in the vessel wall could promote leukocyte adhesion (Cohnheim, J., *Lectures in General Pathology*. (New Syndenham Society, London) Vol. 1, 2nd Ed. (1898)), until recently, potential mechanisms and modulators of this interaction have remained undefined (Harlan, J. M., *Blood*. 65:513-525 (1985)). Certain inflammatory/immune cytokines including interleukin-1 (IL-1) and tumor necrosis factor (TNF), as well as bacterial endotoxin, have been shown to act directly on cultured human vascular endothelium to increase the adhesiveness of its surface for blood leukocytes and related cell lines. Bevilacqua, M. P. et al., *J. Clin. Invest.* 76:2003-2011 (1985); Bevilacqua, M. P. et al., *Am. J. Pathol.* 121:393-403 (1985); Bevilacqua, M. P. et al., *Leukocyte Emigration and Its Sequelae*, Movat, H. Z. (ed.), Karger, N.Y., pp. 79-93 (1987); Gamble, J. R. et al. *Proc Natl. Acad. Sci. teu(USA)* 82:8667-8671 (1985); Schleimer, R. P. et al., *J. Immunol.* 136:649-654 (1986); Dunn, C. J. et al., *The Physiologic, Metabolic and Immunologic Actions of Interleukin*-1, Kluger, M. J. et al., (eds.), Liss, N.Y. pp. 45-54 (1985); Cavender, D. E. et al., *J. Immunol.* 136:203-207 (1986); Yu, C. -L. et al., *J. Immunol.* 136:571 (1986); and Pohlman, T. H. et al., *J. Immunol.* 136:4548-4553 (1986).

A number of leukocyte and endothelial cell surface proteins participate in endothelial cell-leukocyte adhesion. One example, ICAM-1, is expressed on a variety of hemopoetic cells and non-hemopoietic cells including vascular endothelium. ICAM-1 is a 90 kD glycoprotein which is induced by certain cytokines on endothelial cells. ICAM-1 expression is protein-and mRNA sythesis-dependent and its induction is reversible. Dustin, M. L., et al., *J. Immunol.* 137:245-254 (1986); Rothlein, R., et al., *J. Immunol.* 137:1270-1274 (1986); and Pober, J. S., et al., *J. Immunol.* 136:1680-1687 (1986).

A leukocyte cell surface glycoprotein, LFA-1, is expressed on lymphocytes, granulocytes, monocytes, phagocytes and B cells. LFA-1 also plays a role in leukocyte-endothelial cell adhesion. LFA-1 is a dimeric molecule with a 177 kD (alpha or heavy) subunit and a 95 kD (beta or light) subunit. An F(ab')2 Mab has been developed to the alpha and beta subunits which effectively inhibits leukocyte adhesion to endothelial cells. Mentzer, S. J. et al., *J. Cell. Physiol.* 126:285-290 (1986); Mentzer, S. J. et al., *J. Cell. Physiol.* 130:410-415 (1987); and Pohlman, J. H., et al., *J. Immunol.* 136:4548-4553 (1986).

SUMMARY OF THE INVENTION

The invention relates to a cloned gene or degenerant variant thereof, which encodes an endothelial-leukocyte adhesion molecule (ELAM), in particular, ELAM-1 or a fragment thereof.

The cloned gene of the invention comprises the following DNA sequence:

```
   1 CCTGAGACAG AGGCAGCAGT GATACCCACC TGAGAGATCC TGTGTTTGAA
  51 CAACTGCTTC CCAAAACGGA AAGTATTTCA AGCCTAAACC TTTGGGTGAA
 101 AAGAACTCTT GAAGTCATGA TTGCTTCACA GTTTCTCTCA GCTCTCACTT
 151 TGGTGCTTCT CATTAAAGAG AGTGGAGCCT GGTCTTACAA CACCTCCACG
 201 GAAGCTATGA CTTATGATGA GGCCAGTGCT TATTGTCAGC AAAGGTACAC
 251 ACACCTGGTT GCAATTCAAA ACAAAGAAGA GATTGAGTAC CTAAACTCCA
 301 TATTGAGCTA TTCACCAAGT TATTACTGGA TTGGAATCAG AAAAGTCAAC
 351 AATGTGTGGG TCTGGGTAGG AACCCAGAAA CCTCTGACAG AAGAAGCCAA
 401 GAACTGGGCT CCAGGTGAAC CCAACAATAG GCAAAAAGAT GAGGACTGCG
 451 TGGAGATCTA CATCAAGAGA GAAAAAGATG TGGGCATGTG GAATGATGAG
 501 AGGTGCAGCA AGAAGAAGCT TGCCCTATGC TACACAGCTG CCTGTACCAA
 551 TACATCCTGC AGTGGCCACG GTGAATGTGT AGAGACCATC AATAATTACA
 601 CTTGCAAGTG TGACCCTGGC TTCAGTGGAC TCAAGTGTGA GCAAATTGTG
 651 AACTGTACAG CCCTGGAATC CCCTGAGCAT GGAAGCCTGG TTTGCAGTCA
 701 CCCACTGGGA AACTTCAGCT ACAATTCTTC CTGCTCTATC AGCTGTGATA
 751 GGGGTTACCT GCCAAGCAGC ATGGAGACCA TGCAGTGTAT GTCCTCTGGA
 801 GAATGGAGTG CTCCTATTCC AGCCTGCAAT GTGGTTGAGT GTGATGCTGT
 851 GACAAATCCA GCCAATGGGT TCGTGGAATG TTTCCAAAAC CCTGGAAGCT
 901 TCCCATGGAA CACAACCTGT ACATTTGACT GTGAAGAAGG ATTTGAACTA
 951 ATGGGAGCCC AGAGCCTTCA GTGTACCTCA TCTGGGAATT GGGACAACGA
1001 GAAGCCAACG TGTAAAGCTG TGACATGCAG GGCCGTCCGC CAGCCTCAGA
1051 ATGGCTCTGT GAGGTGCAGC CATTCCCCTG CTGGAGAGTT CACCTTCAAA
1101 TCATCCTGCA ACTTCACCTG TGAGGAAGGC TTCATGTTGC AGGGACCAGC
1151 CCAGGTTGAA TGCACCACTC AAGGGCAGTG GACACAGCAA ATCCCAGTTT
1201 GTGAAGCTTT CCAGTGCACA GCCTTGTCCA ACCCCGAGCG AGGCTACATG
1251 AATTGTCTTC CTAGTGCTTC TGGCAGTTTC CGTTATGGGT CCAGCTGTGA
1301 GTTCTCCTGT GAGCAGGGTT TTGTGTTGAA GGGATCCAAA AGGCTCCAAT
1351 GTGGCCCCAC AGGGGAGTGG GACAACGAGA GCCCACATG TGAAGCTGTG
1401 AGATGCGATG CTGTCCACCA GCCCCCGAAG GGTTTGGTGA GGTGTGCTCA
1451 TTCCCCTATT GGAGAATTCA CCTACAAGTC CTCTTGTGCC TTCAGCTGTG
1501 AGGAGGGATT TGAATTATAT GGATCAACTC AACTTGAGTG CACATCTCAG
1551 GGACAATGGA CAGAAGAGGT TCCTTCCTGC CAAGTGGTAA AATGTTCAAG
1601 CCTGGCAGTT CCGGGAAAGA TCAACATGAG CTGCAGTGGG GAGCCCGTGT
1651 TTGGCACTGT GTGCAAGTTC GCCTGTCCTG AAGGATGGAC GCTCAATGGC
1701 TCTGCAGCTC GGACATGTGG AGCCACAGGA CACTGGTCTG GCCTGCTACC
1751 TACCTGTGAA GCTCCCACTG AGTCCAACAT TCCCTTGGTA GCTGGACTTT
1801 CTGCTGCTGG ACTCTCCCTC CTGACATTAG CACCATTTCT CCTCTGGCTT
```

-continued
```
1851 CGGAAATGCT TACGGAAAGC AAAGAAATTT GTTCCTGCCA GCAGCTGCCA
1901 AAGCCTTGAA TCAGACGGAA GCTACCAAAA GCCTTCTTAC ATCCTTTAAG
1951 TTCAAAAGAA TCAGAAACAG GTGCATCTGG GGAACTAGAG GGATACACTG
2001 AAGTTAACAG AGACAGATAA CTCTCCTCGG GTCTCTGGCC CTTCTTGCCT
2051 ACTATGCCAG ATGCCTTTAT GGCTGAAACC GCAACACCCA TCACCACTTC
2101 AATAGATCAA AGTCCAGCAG GCAAGGACGG CCTTCAACTG AAAAGACTCA
2151 GTGTTCCCTT TCCTACTCTC AGGATCAAGA AAGTGTTGGC TAATGAAGGG
2201 AAAGGATATT TTCTTCCAAG CAAAGGTGAA GAGACCAAGA CTCTGAAATC
2251 TCAGAATTCC TTTTCTAACT CTCCCTTGCT CGCTGTAAAA TCTTGGCACA
2301 GAAACACAAT ATTTTGTGGC TTTCTTTCTT TTGCCCTTCA CAGTGTTTCG
2351 ACAGCTGATT ACACAGTTGC TGTCATAAGA ATGAATAATA ATTATCCAGA
2401 GTTTAGAGGA AAAAAATGAC TAAAAATATT ATAACTTAAA AAAATGACAG
2451 ATGTTGAATG CCCACAGGCA AATGCATGGA GGGTTGTTAA TGGTGCAAAT
2501 CCTACTGAAT GCTCTGTGCG AGGGTTACTA TGCACAATTT AATCACTTTC
2551 ATCCCTATGG GATTCAGTGC TTCTTAAAGA GTTCTTAAGG ATTGTGATAT
2601 TTTTACTTGC ATTGAATATA TTATAATCTT CCATACTTCT TCATTCAATA
2651 CAAGTGTGGT AGGGACTTAA AAAACTTGTA AATGCTGTCA ACTATGATAT
2701 GGTAAAAGTT ACTTATTCTA GATTACCCCC TCATTGTTTA TTAACAAATT
2751 ATGTTACATC TGTTTTAAAT TTATTTCAAA AAGGGAAACT ATTGTCCCCT
2801 AGCAAGGCAT GATGTTAACC AGAATAAAGT TCTGAGTGTT TTTACTACAG
2851 TTGTTTTTTG AAAACATGGT AGAATTGGAG AGTAAAAACT GAATGGAAGG
2901 TTTGTATATT GTCAGATATT TTTTCAGAAA TATGTGGTTT CCACGATGAA
2951 AAACTTCCAT GAGGCCAAAC GTTTTGAACT AATAAAAGCA TAAATGCAAA
3001 CACACAAAGG TATAATTTTA TGAATGTCTT TGTTGGAAAA GAATACAGAA
3051 AGATGGATGT GCTTTGCATT CCTACAAAGA TGTTTGTCAG ATGTGATATG
3101 TAAACATAAT TCTTGTATAT TATGGAAGAT TTTAAATTCA CAATAGAAAC
3151 TCACCATGTA AAAGAGTCAT CTGGTAGATT TTTAACGAAT GAAGATGTCT
3201 AATAGTTATT CCCTATTTGT TTTCTTCTGT ATGTTAGGGT GCTCTGGAAG
3251 AGAGGAATGC CTGTGTGAGC AAGCATTTAT GTTTATTTAT AAGCAGATTT
3301 AACAATTCCA AAGGAATCTC CAGTTTTCAG TTGATCACTG GCAATGAAAA
3351 ATTCTCAGTC AGTAATTGCC AAAGCTGCTC TAGCCTTGAG GAGTGTGAGA
3401 ATCAAAACTC TCCTACACTT CCATTAACTT AGCATGTGTT GAAAAAAAAA
3451 GTTTCAGAGA AGTTCTGGCT GAACACTGGC AACGACAAAG CCAACAGTCA
3501 AAACAGAGAT GTGATAAGGA TCAGAACAGC AGAGGTTCTT TTAAAGGGGC
3551 AGAAAAACTC TGGGAAATAA GAGAGAACAA CTACTGTGAT CAGGCTATGT
3601 ATGGAATACA GTGTTATTTT CTTTGAAATT GTTTAAGTGT TGTAAATATT
3651 TATGTAAACT GCATTAGAAA TTAGCTGTGT GAAATACCAG TGTGGTTTGT
3701 GTTTGAGTTT TATTGAGAAT TTTAAATTAT AACTTAAAAT ATTTTATAAT
3751 TTTTAAAGTA TATATTTATT TAAGCTTATG TCAGACCTAT TTGACATAAC
3801 ACTATAAAGG TTGACAATAA ATGTGCTTAT GTTTAAAAAA AAAAAAAAAA
3851 AAAA
```

The invention also relates to a clones gene comprising the ELAM-1 coding sequence having the following DNA sequence:

```
    ATGA TTGCTTCACA GTTTCTCTCA GCTCTCACTT
151 TGGTGCTTCT CATTAAAGAG AGTGGAGCCT GGTCTTACAA CACCTCCACG
201 GAAGCTATGA CTTATGATGA GGCCAGTGCT TATTGTCAGC AAAGGTACAC
251 ACACCTGGTT GCAATTCAAA ACAAAGAAGA GATTGAGTAC CTAAACTCCA
301 TATTGAGCTA TTCACCAAGT TATTACTGGA TTGGAATCAG AAAAGTCAAC
351 AATGTGTGGG TCTGGGTAGG AACCCAGAAA CCTCTGACAG AAGAAGCCAA
401 GAACTGGGCT CCAGGTGAAC CCAACAATAG GCAAAAAGAT GAGGACTGCG
451 TGGAGATCTA CATCAAGAGA GAAAAAGATG TGGGCATGTG GAATGATGAG
501 AGGTGCAGCA AGAAGAAGCT TGCCCTATGC TACACAGCTG CCTGTACCAA
551 TACATCCTGC AGTGGCCACG GTGAATGTGT AGAGACCATC AATAATTACA
601 CTTGCAAGTG TGACCCTGGC TTCAGTGGAC TCAAGTGTGA GCAAATTGTG
651 AACTGTACAG CCCTGGAATC CCCTGAGCAT GGAAGCCTGG TTTGCAGTCA
701 CCCACTGGGA AACTTCAGCT ACAATTCTTC CTGCTCTATC AGCTGTGATA
751 GGGGTTACCT GCCAAGCAGC ATGGAGACCA TGCAGTGTAT GTCCTCTGGA
801 GAATGGAGTG CTCCTATTCC AGCCTGCAAT GTGGTTGAGT GTGATGCTGT
851 GACAAATCCA GCCAATGGGT TCGTGGAATG TTTCCAAAAC CCTGGAAGCT
901 TCCCATGGAA CACAACCTGT ACATTTGACT GTGAAGAAGG ATTTGAACTA
951 ATGGGAGCCC AGAGCCTTCA GTGTACCTCA TCTGGGAATT GGGACAACGA
```

-continued

1001 GAAGCCAACG TGTAAAGCTG TGACATGCAG GGCCGTCCGC CAGCCTCAGA

1051 ATGGCTCTGT GAGGTGCAGC CATTCCCCTG CTGGAGAGTT CACCTTCAAA

1101 TCATCCTGCA ACTTCACCTG TGAGGAAGGC TTCATGTTGC AGGGACCAGC

1151 CCAGGTTGAA TGCACCACTC AAGGGCAGTG GACACAGCAA ATCCCAGTTT

1201 GTGAAGCTTT CCAGTGCACA GCCTTGTCCA ACCCCGAGCG AGGCTACATG

1251 AATTGTCTTC CTAGTGCTTC TGGCAGTTTC CGTTATGGGT CCAGCTGTGA

1301 GTTCTCCTGT GAGCAGGGTT TTGTGTTGAA GGGATCCAAA AGGCTCCAAT

1351 GTGGCCCCAC AGGGGAGTGG GACAACGAGA AGCCCACATG TGAAGCTGTG

1401 AGATGCGATG CTGTCCACCA GCCCCCGAAG GGTTTGGTGA GGTGTGCTCA

1451 TTCCCCTATT GGAGAATTCA CCTACAAGTC CTCTTGTGCC TTCAGCTGTG

1501 AGGAGGGATT TGAATTATAT GGATCAACTC AACTTGAGTG CACATCTCAG

1551 GGACAATGGA CAGAAGAGGT TCCTTCCTGC CAAGTGGTAA AATGTTCAAG

1601 CCTGGCAGTT CCGGGAAAGA TCAACATGAG CTGCAGTGGG GAGCCCGTGT

1651 TTGGCACTGT GTGCAAGTTC GCCTGTCCTG AAGGATGGAC GCTCAATGGC

1701 TCTGCAGCTC GGACATGTGG AGCCACAGGA CACTGGTCTG GCCTGCTACC

1751 TACCTGTGAA GCTCCCACTG AGTCCAACAT TCCCTTGGTA GCTGGACTTT

1801 CTGCTGCTGG ACTCTCCCTC CTGACATTAG CACCATTTCT CCTCTGGCTT

1851 CGGAAATGCT TACGGAAAGC AAAGAAATTT GTTCCTGCCA GCAGCTGCCA

1901 AAGCCTTGAA TCAGACGGAA GCTACCAAAA GCCTTCTTAC ATCCTTTAA the invention also relates to ELAM-1, obtained by expressing the cloned gene of the invention, comprising the following amino acid sequence:

```
                        M I
A S Q F L S A L T L V L L I K E S G A W
S Y N T S T E A M T Y D E A S A Y C Q Q
R Y T H L V A I Q N K E E I E Y L N S I
L S Y S P S Y Y W I G I R K V N N V W V
W V G T Q K P L T E E A K N W A P G E P
N N R Q K D E D C V E I Y I K R E K D V
G M W N D E R C S K K K L A L C Y T A A
C T N T S C S G H G E C V E T I N N Y T
C K C D P G F S G L K C E Q I V N C T A
L E S P E H G S L V C S H P L G N F S Y
N S S C S I S C D R G Y L P S S M E T M
Q C M S S G E W S A P I P A C N V V E C
D A V T N P A N G F V E C F Q N P G S F
P W N T T C T F D C E E G F E L M G A Q
S L Q C T S S G N W D N E K P T C K A V
T C R A V R Q P Q N G S V R C S H S P A
G E F T F K S S C N F T C E E G F M L Q
G P A Q V E C T T Q G Q W T Q Q I P V C
E A F Q C T A L S N P E R G Y M N C L P
S A S G S F R Y G S S C E F S C E Q G F
V L K G S K R L Q C G P T G E W D N E K
P T C E A V R C D A V H Q P P K G L V R
C A H S P I G E F T Y K S S C A F S C E
E G F E L Y G S T Q L E C T S Q G Q W T
E E V P S C Q V V K C S S L A V P G K I
N M S C S G E P V F G T V C K F A C P E
G W T L N G S A A R T C G A T G H W S G
L L P T C E A P T E S N I P L V A G L S
A A G L S L L T L A P F L L W L R K C L
R K A K K F V P A S S C Q S L E S D G S
Y Q K P S Y I L
```

The invention also relates to a cloned gene, or degenerate variant thereof, which encodes a fusion protein comprising ELAM-1, or a fragment thereof, and a second protein which may be diphtheria toxin, ricin or other cytotoxic protein.

The invention also relates to plasmids containing the cloned genes of the invention, hosts transformed with the plasmids of the invention, and ELAM-1 or a fragment thereof expressed by the transformed hosts of the invention.

The invention also relates to fusion proteins comprising ELAM-1, or a fragment thereof, and a second protein which may be diphtheria toxin, ricin or other cytotoxic protein.

The invention also relates to pharmaceutical compositions comprising ELAM-1, or a fragment thereof, and a pharmaceutically acceptable carrier.

The invention also relates to pharmaceutical compositions comprising a fusion protein comprising ELAM-1, or a fragment thereof, and a second protein which may be diphtheria toxin or ricin.

The invention also relates to a method for the treatment of inflammation comprising administering to a patient a pharmaceutical composition comprising ELAM-1, or a fragment thereof.

The invention also relates to a method of preventing or treating post-reperfusion injury comprising administering to a patient a pharmaceutical composition comprising ELAM-1 or a fragment thereof.

The invention also relates to a method for the treatment of leukemia or lymphoma comprising administering to a patient a pharmaceutical composition comprising ELAM-1, or a fragment thereof.

The invention also relates to a treatment for infections (e.g., bacterial, viral or parasitic) comprising administering to a patient a pharmaceutical composition comprising ELAM-1, or a fragment thereof.

The invention also relates to a treatment of vasculitis comprising administering to a patient a pharmaceutical composition comprising ELAM-1, or a fragment thereof.

The invention also relates to a method for inhibiting metastatic spread of tumor cells administering to a patient a pharmaceutical composition comprising ELAM-1 or a fragment thereof, and a pharmaceutically acceptable carrier.

The invention also relates to a method for the treatment of inflammation by administering to a patient a pharmaceutical composition which contains a therapeutically effective amount of an ELAM-1 specific antibody, or and antibody fragment thereof, and a pharmaceutically acceptable carrier.

The invention also relates to a method for the treatment of infection (e.g., bacterial, viral or parasitic), comprising administering to a patient a pharmaceutical composition comprising a therapeutically effective amount of an ELAM-1 specific antibody, or antibody fragment, and a pharmaceutically acceptable carrier.

DESCRIPTION OF THE PREFERRED EMBODIMENTS

ELAM-1 is an endothelial cell surface glycoprotein which participates in endothelial-leukocyte adhesion. This adhesion protein is induced by certain cytokines. ELAM-1 is identified by specific binding of murine Mab (H4/18 and H18/7) developed against stimulated endothelial cells. The time sequence of induction of the antigen recognized by H4/18 and H18/7 binding antigens and the susceptibility of its expression to metabolic inhibitors were similar to those observed for leukocyte adhesion. Bevilacqua, M. P., et al., *4th Int'l Symp. Biol. Vasc. Endothelial Cell:*13 (Abstr) (1986); Pober, J. S., et al., *J. Immunol.* 136:1680-1687 (1986); Bevilacqua, M. P. et al., *Proc. Natl. Acad. Sci. (USA)* 84:9238-9242 (1987); Bevilacqua, M. P., et al., in: *Leukocyte Immigration and Its Sequelae, Satellite Symp.* (Henry Z. Movat, ed.), pp. 79-93, published by S. Karger, Basil, Switzerland (1987). These putative endothelial cell surface structures were termed "endothelial-leukocyte adhesion molecules" (ELAMs). Expression of ELAM-1 by stimulated endothelial cells was blocked by protein and RNA synthesis inhibitors, but not by cyclooxygenase inhibitors. The H4/18 Mab immunoprecipitated two biosynthetically labeled polypeptides with molecular weights of 100 kD and 120 kD. H4/18 and F(ab')2 fragments were found to partially inhibit HL-60 cell (premyelocytic cell line) adhesion to activated HEC, but did not affect the adhesion of normal blood cells. In contrast, Mab H18/7 did block the adhesion of normal blood PMN and therefore allowed the designation of ELAM-1 (Bevilacqua et al., *Proc. Natl. Acad. Sci. (USA)* 84:9238-9242 (1987).

Induction of expression of ELAM-1 on endothelial cells at the site of inflammation has been detected at the site of inflammation using the Mab H4/18 in microvascular endothelium of human skin. Cotran, R. S., et al., *J. Exp. Med.* 164:661-666 (1986).

The present invention relates to cloned ELAM-1 genes. cDNA encoding ELAM-1 may be obtained by stimulating cultured human endothelium cells, isolation of the mRNA, followed by preparation of cDNA by, for example, use of reverse transcriptase according to methods known in the art. Alternatively, episomal DNA may be recovered. The cDNA or episomal DNA is then shotgun cloned, and the resulting clones screened with an antibody which recognizes ELAM-1. Alternatively, the clones may be screened with a complementary labeled probe.

Antibodies which recognize ELAM-1 may be prepared by immunizing mice with cultured human endothelial cells (HEC) which have been activated by, for example, the monokine interleukin 1 (IL 1). Fusion of the splenocytes with myeloma cells and subsequent screening of the hybridomas with IL 1-treated and control HEC allows selection of monoclonal antibodies specific for ELAM-1. See Bevilacqua, M. P., et al., *4th Int'l Symp. Biol. Vasc. Endothelial Cell:*13 (Abstr) (1986); Pober, J. S., et al., *J. Immunol.* 136:1680-1687 (1986); Bevilacqua, M. P., et al., in: *Leukocyte Immigration and Its Sequelae, Satellite Symp.* (Henry Z. Movat, ed.), pp. 79-93, published by S. Karger, Basil, Switzerland (1987). Bevilacqua et al., *Proc. Natl. Acad. Sci. (USA)* 84:9238-9242 (1987). Particularly useful monoclonal antibodies for this purpose include H 4/18 and H 18/7.

Antibodies to ELAM-1 may also be prepared by immunizing mice with recombinant ELAM-1, or ELAM-1 fragments. By "ELAM-1 fragment" is intended any polypeptide subset of the molecule. Particularly preferred ELAM-1 fragments include leukocyte-binding fragments and complement-binding fragments. The leukocyte-binding or complement-binding fragments may be obtained by cutting the ELAM-1 gene with various restriction enzymes or exonucleases, cloning the resulting fragments, and screening for leukocyte or complement binding activity according to methods known in the art. Alternatively, it is possible to analyze the ELAM-1 structure by a suitable computer program, identify the antigenic regions, and prepare ELAM-1 fragments by methods of protein synthesis known to those of ordinary skill in the art. Therefore, the invention also relates to antibodies having defined specificity obtained by immunization of an animal with an ELAM-1 fragment.

The joining of various DNA fragments, is performed in accordance with conventional techniques, employing blunt-ended or staggered-ended termini for ligation, restriction enzyme digestion to provide appropriate termini, filling in of cohesive ends as appropriate, alkali and phosphatase treatment to avoid undesirable joining, and ligation with appropriate ligases. The genetic construct may optionally encode a leader sequence to allow efficient expression of the recombinant protein.

To express the recombinant ELAM-1, transcriptional and translational signals recognized by an appropriate host element are necessary. Mammalian cells provide post translational modification to recombinant protein molecules which provide for correct folding and glycosylation of appropriate sites. Mammalian cells which may be used in the practice of the invention include COS cells, Chinese hamster ovary (CHO) cells, leukocytes, myeloma cells or other transformed or oncogenic lymphocytes, e.g., EBV-transformed cells, cells of fibroblast origin such as VERO or cells of lymphoid origin, such as the hybridoma SP2/O-AG14 or the myeloma P3x63Sgh, and their derivatives. Other hosts include BHK cells and hepatoma cells.

In general, vectors containing replicon and control sequences which are derived from species compatible with a host cell are used in connection with the host. The vector ordinarily carries a replicon site, as well as specific genes which are capable of providing phenotypic selection in transformed cells. The expression of the gene-encoding ELAM-1 can also be placed under control with other regulatory sequences which may be homologous to the cell line in its untransformed state. For example, lactose-dependent *E. coli* chromosomal DNA comprises a lactose or lac operon which mediates lactose utilization by elaborating the enzyme beta-galactosidase. The lac control elements may be obtained from bacterial phage lambda plac5, which is infective for *E. coli*. The lac promoter-operator system can be induced by IPTG.

Other promoters/operator systems or portions thereof can be employed as well. For example, colicin E1, galactose, alkaline phosphatase, tryptophan, xylose, and the like can be used.

For mammalian hosts, several possible vector systems are available for expression. One class of vectors utilize DNA elements which are derived from animal viruses such as bovine papilloma virus, polyoma virus, adenovirus, vaccinia virus, baculovirus, retroviruses (RSV, MMTV or MOMLV), or SV40 virus. Cells which have stably integrated the DNA into their chromosomes may be selected by introducing one or more markers which allow selection of transfected host cells. The marker may provide for prototropy to an auxotrophic host, biocide resistance, e.g., antibiotics, or heavy metals such as copper or the like. The selectable marker gene can be either directly linked to the DNA sequences to be expressed, or introduced into the same cell by cotransformation. Additional elements may also be needed for optimal synthesis of mRNA. These elements may include splice signals, as well as transcriptional promoters, enhancers, and termination signals. The cDNA expression vectors incorporating such elements includes those described by Okayama, H., *Mol. Cel. Biol.*, 3:280 (1983) and others.

Once the vector or DNA sequence containing the constructs has been prepared for expression, the DNA constructs may be introduced to an appropriate host. Various techniques may be employed, such as protoplast fusion, calcium phosphate precipitation, electroporation or other conventional techniques. After transfection, the cells are grown in media and screened for the appropriate activity using, for example, the above-described antibodies. Expression of the gene(s) results in production of the ELAM-1.

The transformed cells may be grown in appropriate nutrient medium in culture flasks or injected into a synergistic host, e.g., mouse or a rat, or immunodeficient host or host site, e.g., nude mouse or hamster pouch. In particular, the cells may be introduced into the abdominal cavity of an animal to allow production of ascites fluid which contains ELAM-1, or fragment thereof. Alternatively, the cells may be injected subcutaneously and ELAM-1 is harvested from the blood of the host. The cells may be used in the same manner as hybridoma cells.

The expressed ELAM-1, or fragment thereof, may be isolated from fermentation media or cell culture and purified in accordance with conventional conditions, such as extraction, precipitation, chromatography, affinity chromatography, electrophoresis or the like.

For example, ELAM-1 may be purified by passing a solution containing the surface protein through a column containing an immobilized antibody which is specific for ELAM-1, for example, the above-described antibodies H18/7 and H4/18. The desired protein may then be eluted by raising the pH of the eluant.

ELAM-1, or fragments thereof, may be administered to a patient to treat inflammation. A soluble form of ELAM-1 may block leukocyte adhesion to endothelium at sites of inflammation. In addition, the primary structure of ELAM-1 derived from amino acid sequence analysis suggests that ELAM-1 binds proteins of the complement system. Therefore, administration of ELAM-1, or the complement or leukocyte-binding fragment thereof, would regulate complement activation and inhibit its pathophysiological consequences.

It is also possible to block inflammation by administering to a patient a monoclonal antibody directed toward ELAM-1. Such monoclonal antibodies include the above-described antibodies H18/7 and H4/18. The monoclonal antibodies may also comprise antibody fragments, for example, F(ab')2 fragments which minimize immunological reaction due to the Fc portion of the immunoglobin.

Administration of ELAM-1, or fragment thereof, may also be used for the prevention of post-reperfusion injury. When treating arterial thrombosis, induction of reperfusion by clot lysing agents such as tissue plasminogen activator (t-PA) is often associated with tissue damage. Such tissue damage is thought to be mediated, at least in part by polymorphonuclear leukocytes (PMN). Therefore, administration of ELAM-1, or a fragment thereof, preferably, a leukocyte-binding fragment, would block PMN-endothelial interactions, and thereby diminish or prevent post-reperfusion injury.

Alternatively, it is also possible to administer an antibody to a patient directed toward ELAM-1 to block PMN-endothelial interactions, and thereby prevent or treat inflammation. Suitable antibodies for this purpose include H18/7 and H4/18, or an antibody fragment thereof.

It is also possible to use antibodies directed to ELAM-1 to detect the presence of ELAM-1 in biological fluids such as blood, serum, cerebrospinal fluid, etc., as an indication of expression of ELAM-1 in association with disease processes. Thus, the invention also relates to a method of detecting endothelial cell expression of ELAM-1 in a patient by an assay for ELAM-1, comprising contacting a detectably labeled antibody directed to ELAM-1 with a sample suspected of containing ELAM-1, or cell which expresses ELAM-1 on its surface, and detecting whether a complex has formed.

The detection and quantitation of antigenic substances and biological samples frequently utilize immunoassay techniques. These techniques are based upon the formation of a complex between the antigenic substance being assayed, e.g., ELAM-1, and an antibody or antibodies in which one or the other member of the complex may be detectably labeled. In the present invention, the ELAM-1 specific antibody may be labeled with any conventional label.

Thus, in this aspect of the invention, a biological sample may be treated with nitrocellulose, or other solid support which is capable of immobilizing cells, cell particles or soluble protein. The support may then be washed with suitable buffers followed by treatment with the detectably labeled ELAM-1 specific antibody. The solid phase support may then be washed with the buffer a second time to remove unbound antibody. The amount of bound label on the antibody may then be detected by conventional means.

In carrying out the assay of the present invention on a sample containing ELAM-1 or cells expressing ELAM-1 on their surface, the process comprises:

(a) contacting a sample suspected containing ELAM-1 or cell expressing ELAM-1 on its surface with a solid support to effect immobilization of ELAM-1, or cell which expresses ELAM-1 on its surface;

(b) contacting said solid support with a detectably labeled ELAM-1 specific antibody;

(c) incubating said detectably labeled ELAM-1 specific antibody with said support for a time sufficient to allow the ELAM-1 specific antibody to bind to the immobilized ELAM-1 or cell which expresses ELAM-1 on its surface;

(d) separating the solid phase support from the incubation mixture obtained in step (c); and (e) detecting the bound label and thereby detecting and quantifying ELAM-1 or cell expressing ELAM-1 on its surface.

Alternatively, labeled ELAM-1 specific antibody/ELAM-1 complex in a sample may be separated from a reaction mixture by contacting the complex with an immobilized antibody or protein which is specific for an immunoglobulin, e.g., protein A, protein G, anti-IgM or anti-IgG antibodies. Such anti-immunoglobulin antibodies may be monoclonal or polyclonal. The solid support may then be washed with a suitable buffer to give an immobilized ELAM-1/labeled ELAM-1 specific antibody complex. The label on the fusion protein may then be detected to give a measure of endogenous ELAM-1 and, thereby, the extent of stimulated endothelial cells.

This aspect of the invention relates to a method for detecting ELAM-1 or leukocyte-binding fragment thereof in a sample comprising (a) contacting a sample suspected of containing ELAM-1 with an ELAM-1 specific antibody or fragment thereof which binds to ELAM-1;

(b) detecting whether a complex is formed.

The invention also relates to a method of detecting ELAM-1 in a sample, further comprising (c) contacting the mixture obtained in step (a) with an Fc binding molecule, such as an antibody, protein A, or protein G, which is immobilized on a solid phase support and is specific for the ELAM-1 specific antibody to give a ELAM-1/ELAM-1 specific antibody-immobilized antibody complex;

(d) washing the solid phase support obtained in step (c) to remove unbound ELAM-1/ELAM-1 specific antibody complex;

(e) and detecting the label on the ELAM-1 specific antibody.

Of course, the specific concentrations of detectably labeled antibody and ELAM-1, the temperature and time of incubation, as well as other assay conditions may be varied, depending on various factors including the concentration of ELAM-1 in the sample, the nature of the sample, and the like. Those skilled in the art will be able to determine operative and optimal assay conditions for each determination by employing routine experimentation.

Other such steps as washing, stirring, shaking, filtering and the like may be added to the assays as is customary or necessary for the particular situation.

One of the ways in which the ELAM-1 specific antibody can be detectably labeled is by linking the same to an enzyme. This enzyme, in turn, when later exposed to its substrate, will react with the substrate in such a manner as to produce a chemical moiety which can be detected, for example, by spectrophotometric, fluorometric or by visual means. Enzymes which can be used to detectably label the ELAM-1 specific antibody include, but are not limited to, malate dehydrogenase, staphylococcal nuclease, delta-V-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-VI-phosphate dehydrogenase, glucoamylase and acetylcholine esterase.

The ELAM-1 specific antibody may also be labeled with a radioactive isotope which can be determined by such means as the use of a gamma counter or a scintillation counter or by audioradiography. Isotopes which are particularly useful for the purpose of the present invention are: $^{3}H$, $^{125}I$, $^{131}I$, $^{32}P$, $^{35}S$, $^{14}C$, $^{51}Cr$, $^{36}Cl$, $^{57}Co$, $^{58}Co$, $^{59}Fe$ and $^{75}Se$.

It is also possible to label the ELAM-1 specific antibody with a fluorescent compound. When the fluorescently labeled antibody is exposed to light of the proper wave length, its presence can then be detected due to the fluorescence of the dye. Among the most commonly used fluorescent labelling compounds are fluorescein isothiocyanate, rhodamine, phycoerytherin, phycocyanin, allophycocyanin, o-phthaldehyde and fluorescamine.

The ELAM-1 specific antibody can also be detectably labeled using fluorescence emitting metals such as $^{152}Eu$, or others of the lanthanide series. These metals can be attached to the ELAM-1 specific antibody using such metal chelating groups as diethylenetriaminepentaacetic acid (DTPA) or ethylenediaminetetraacetic acid (EDTA).

The ELAM-1 specific antibody also can be detectably labeled by coupling it to a chemiluminescent compound. The presence of the chemiluminescent-tagged ELAM-1 specific antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the ELAM-1 specific antibody of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

Detection of the ELAM-1 specific antibody may be accomplished by a scintillation counter, for example, if the detectable label is a radioactive gamma emitter, or by a fluorometer, for example, if the label is a fluorescent material. In the case of an enzyme label, the detection can be accomplished by colorimetric methods which employ a substrate for the enzyme. Detection may also be accomplished by visual comparison of the extent of enzymatic reaction of a substrate in comparison with similarly prepared standards.

ELAM-1, or leukocyte-binding fraction thereof, may also be administered to a patient to prevent adhesion of leukocyte tumor cells or non-leukocyte tumor cells to endothelial tissue. Thus, administration of ELAM-1, or leukocyte-binding fragment thereof, would prevent metastatic spread of tumor cells. Alternatively, antibodies directed to ELAM-1, or antibody fragments, may be administered to block the adhesion of tumor cells to endothelial tissue, thereby inhibiting metastatic spread.

In addition, ELAM-1, or a leukocyte-binding fragment thereof, may be coupled to a chemotherapeutic drug which could bind to tumor cells expressing receptors for ELAM-1, to kill the tumor cell. Thus, the invention also relates to a method for treating, for example, leukemia comprising administering to a patient ELAM-1, or a leukocyte-binding fragment thereof, which is coupled to an anti-tumor agent. Such antitumor agents may include, for example, bacterial toxins such as diphtheria toxin or ricin, a toxic lectin.

Thus, the invention also relates to fusion proteins comprising ELAM-1, or leukocyte-binding fragment thereof, coupled to a second protein comprising diphtheria toxin or ricin. Methods for producing fusion proteins comprising fragment A of diphtheria toxin by recombinant means are taught in U.S. Pat. No. 4,675,382 (1987). Diphtheria toxin contains two polypeptide chains. The B chain binds the toxin to a receptor on a cell surface. The A chain actually enters the cytoplasm and inhibits protein synthesis by inactivating elongation factor 2, the factor that translocates ribosomes along mRNA concomitant with hydrolysis of ATP. See Darnell, J., et al., in *Molecular Cell Biology*, Scientific American Books, Inc., page 662 (1986). In a preferred embodiment, the fusion protein of the invention comprises ELAM-1, or a leukocyte-binding fragment thereof, and the A chain of diphtheria toxin.

ELAM-1 is also useful for the treatment of microbial infections. A variety of microbes (bacteria, rickettsia, borrelia, various parasites, and viruses) bind to vascular endothelium in some cases, possibly, by an ELAM-1 dependent mechanism. Thus, ELAM-1, or a leukocyte-binding fragment thereof, may be administered to a patient to prevent the binding of microbes which recognize ELAM-1 as a binding target molecule and thereby, treat microbial infections.

Moreover, it is also possible to administer an antibody or antibody fragment directed to ELAM-1, to block the microbe receptor on endothelial tissue. Thus, the invention also relates to the treatment of microbial infections comprising administering an antibody, or antibody fragment, directed to ELAM-1 to a patient.

The invention also relates to a treatment for microbial infections comprising administering a pharmaceutical composition comprising ELAM-1, or a fragment thereof, which is coupled to an antimicrobial agent. Such a conjugate specifically delivers and localizes the antimicrobial agent at the site of vascular infection.

Such antimicrobial agents include ricin or diphtheria toxin, as described above, or may comprise halogenated amino acids which act as suicide enzyme inhibitors. See Soper, T. S., et al., *J. Biol. Chem.* 252:3170–3175 (1977) (β-chloroalanine); Kollonitsch, J., et al., *J. Amer. Chem. Soc.* 98:5591–5593 (1976) (3-fluoroalanine); Wang, E., et al., *Biochemistry* 17:1313–1321 (1978) (β,β-difluoroalanine and β,β,β-trifluoroalanine).

The invention also relates to a method of treating vasculitis by administering ELAM-1, or a fragment thereof, to a patient. Recent evidence suggests that tissue damage in certain forms of vasculitis involves induced endothelial surface proteins. Thus, ELAM-1 may be a target for antibody-mediated or cell-mediated damage of the vessel wall.

ELAM-1, or a structurally homologous molecule, may be involved in mediating cell-cell interactions in embryogenesis/organ development; in neoplasia (with possible expression by tumor cells); in wound/tissue regeneration; and in related processes. Therefore, administration of ELAM-1, or fragments thereof, is useful as a therapeutic intervention and/or a diagnostic tool for investigation of these processes.

The ELAM-1 molecule, or fragment thereof, or antibodies and antibody fragments directed to ELAM-1, can be formulated into pharmaceutically useful compositions according to known methods, such as by admixture with a pharmaceutically acceptable carrier vehicle. Suitable vehicles and their formulation are described, for example, in *Remington's Pharmaceutical Sciences* (16th ed.), Osol, A. (ed.), Mack Publishers, Easton (1980). In order to form a pharmaceutically acceptable composition suitable for effective administration, such compositions will contain a therapeutically effective amount of the ELAM-1, fragment of ELAM-1, or antibody or antibody fragment directed to ELAM-1, either alone or with a suitable amount of carrier vehicle.

When used for the treatment of inflammation, post-reperfusion injury, leukemia, lymphoma, microbial/parasitic infection, vasculitis, or inhibition of the metastatic spread of tumor cells, the pharmaceutical composition may comprise from 1 pg/kg to 10 mg/kg patient of ELAM-1, fragment of ELAM-1, or fusion protein of the invention, although higher or lower doses are possible. When used for the purpose of treating inflammation, microbial/parasitic infection, post-reperfusion injury, leukemia, lymphoma, vasculitis or inhibition of the metastatic spread of tumor cells, the pharmaceutical composition may comprise from 1 pg/kg to 10 mg/kg of ELAM-specific antibody or antibody fragment thereof, although higher or lower doses are possible.

Additional pharmaceutical methods may be employed to control the duration of action. Controlled release preparations may be achieved by the use of polymers to complex or absorb the ELAM-1, ELAM-1 fragment or antibody or antibody fragment directed to ELAM-1 of the invention. Controlled delivery may be achieved by selecting appropriate macromolecules (for example, polyesters, polyamino acids, polyvinyl pyrrolidone, ethylenevinylacetate, methylcellulose, carboxymethylcellulose, protamine sulfate, or lactide/glycolide copolymers). The rate of drug release may also be controlled by altering the concentration of such macromolecules. Another possible method for controlling the duration of action comprises incorporating the therapeutic agents into particles of a polymeric substance such as polyesters, polyamino acids, hydrogels, polylactide/glycolide copolymers, or ethylenevinylacetate copolymers. Alternatively, it is possible to entrap the therapeutic agents in microcapsules prepared, for example, by coacervation techniques or by interfacial polymerization, for example, by the use of hydroxymethylcellulose or gelatin-microcapsules or poly(methylmethacrolate) microcapsules, respectively, or in a colloid drug delivery system, for example, liposomes, albumin microspheres, microemulsions, nanoparticles, nanocapsules, or in macroemulsions. Such teachings are disclosed in *Remington's Pharmaceutical Sciences* (1980).

ELAM-1, fragment of ELAM-1, or antibody or antibody fragment directed to ELAM-1 may be provided to a patient by means well known in the art. Such means of introduction include oral means, intranasal means, subcutaneous means, intramuscular means, intravenous means, intra-arterial means, or parenteral means.

Having now generally described this invention, the same will be better understood with reference to certain specific examples which are herein included for purposes of illustration only, and are not intended to be limiting of the invention, unless specified.

EXAMPLES

Example 1

Molecular Cloning of ELAM-1

A cDNA library was constructed using RNA obtained from cultured HEC that had been treated for 2 hr with rIL-1β (5 U/ml). The library was transfected into COS cells and Mabs H18/7 and H4/18 were used to isolate cells expressing ELAM-1 epitopes. Episomal DNA was recovered, expanded in bacteria (mc 1061p3), and subjected to two more rounds of expression-panning (Seed, B., and Aruffo, A., *Proc. Natl. Acad. Sci.* (*USA*) 84:3365-3369 (1987); Aruffo, A., and Seed, B., *Proc. Natl. Acad. Sci.* (*USA*) 84:8573-8577 (1987)) to obtain a cDNA clone designated pELAM-1. COS cells transfected with pELAM-1 expresses a molecule(s) reactive with both Mab H18/7 and H4/18, but not with control Mabs, as detected by indirect immunofluorescence and immunoperoxidase.

Mab H18/7 immunoprecipitated two polypeptides of Mr 115,000 and 97,000 from biosynthetically labeled, rIL-1 stimulated HEC but not from control HEC. Two proteins of similar mass (Mr 107,000 and 97,000) were obtained from biosynthetically labeled, pELAM-1 transfected COS cells. The lower molecular mass of the COS cell product is consistent with previous observations (Seed, B., and Aruffo, A., *Proc. Natl. Acad. Sci.* (*USA*) 84:3365-3369 (1987); Aruffo, A., and Seed, B., *Proc. Natl. Acad. Sci.* (*USA*) 84:8573-8577 (1987)), and may reflect altered glycosylation. Treatment of both the COS cell and HEC derived immunoprecipitates with N-glycosidase F (N-Glycanase, Genzyme Inc., Boston, Mass.) to remove N-linked carbohydrates, yielded a single band by electrophoresis corresponding to a polypeptide(s) of Mr 77,000. These data suggest that the polypeptide backbone of recombinant, COS cell-derived ELAM-1 is equivalent to that of natural, endothelial cell-derived ELAM-1. In addition, it is consistent with the hypothesis that the two species immunoprecipitated from biosynthetically labeled cells contain the same polypeptide backbone and differ in post-translational modification. This hypothesis is further supported by pulse-chase biosynthetic labeling experiments using rIL-1β stimulated HEC and pELAM-1 transfected COS cells. In both cases, label is first seen associated with the lower molecular mass protein (Mr 97,000), followed by an apparent "chasing" of the label into the upper molecular mass form. Taken together, these data strongly suggest that the two species immunoprecipitated with anti-ELAM-1 Mabs are related as precursor and product.

Example 2

Primary Structure and Homologies

Figure 1:
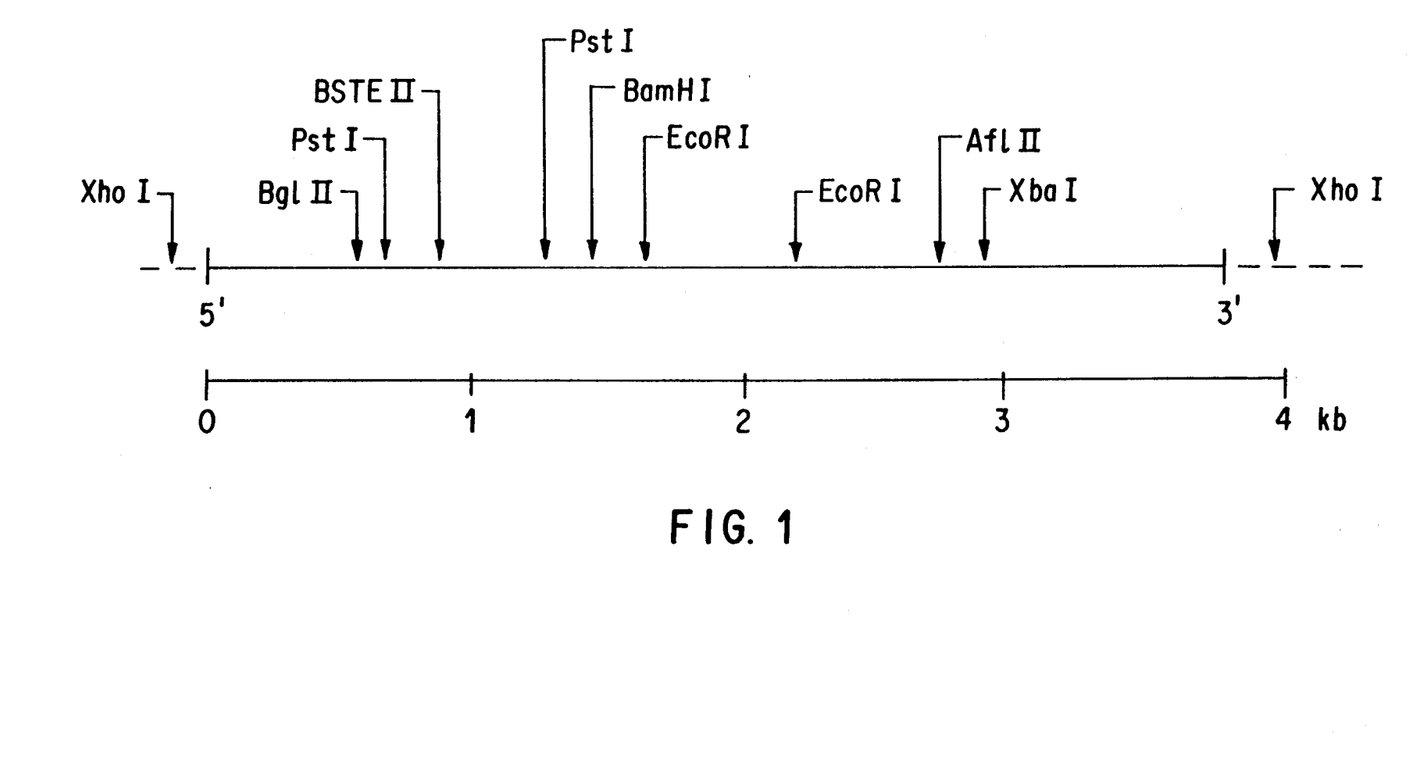
FIG. 1 depicts an enzyme restriction map of ELAM-1 cDNA.

As represented in FIG. 1, pELAM-1 was found to be 3.85 kb with a short 5' untranslated region, a 1,830 base open reading frame, and a relatively long (1.9 kb) 3' untranslated region. The nucleotide sequence of the cDNA encoding ELAM-1 and the 3' untranslated region is shown below:

```
   1 CCTGAGACAG AGGCAGCAGT GATACCCACC TGAGAGATCC TGTGTTTGAA
  51 CAACTGCTTC CCAAAACGGA AAGTATTTCA AGCCTAAACC TTTGGGTGAA
 101 AAGAACTCTT GAAGTCATGA TTGCTTCACA GTTTCTCTCA GCTCTCACTT
 151 TGGTGCTTCT CATTAAAGAG AGTGGAGCCT GGTCTTACAA CACCTCCACG
 201 GAAGCTATGA CTTATGATGA GGCCAGTGCT TATTGTCAGC AAAGGTACAC
 251 ACACCTGGTT GCAATTCAAA ACAAAGAAGA GATTGAGTAC CTAAACTCCA
 301 TATTGAGCTA TTCACCAAGT TATTACTGGA TTGGAATCAG AAAAGTCAAC
 351 AATGTGTGGG TCTGGGTAGG AACCCAGAAA CCTCTGACAG AAGAAGCCAA
 401 GAACTGGGCT CCAGGTGAAC CCAACAATAG GCAAAAAGAT GAGGACTGCG
 451 TGGAGATCTA CATCAAGAGA GAAAAAGATG TGGGCATGTG GAATGATGAG
 501 AGGTGCAGCA AGAAGAAGCT TGCCCTATGC TACACAGCTG CCTGTACCAA
 551 TACATCCTGC AGTGGCCACG GTGAATGTGT AGAGACCATC AATAATTACA
 601 CTTGCAAGTG TGACCCTGGC TTCAGTGGAC TCAAGTGTGA GCAAATTGTG
 651 AACTGTACAG CCCTGGAATC CCCTGAGCAT GGAAGCCTGG TTTGCAGTCA
 701 CCCACTGGGA AACTTCAGCT ACAATTCTTC CTGCTCTATC AGCTGTGATA
 751 GGGGTTACCT GCCAAGCAGC ATGGAGACCA TGCAGTGTAT GTCCTCTGGA
 801 GAATGGAGTG CTCCTATTCC AGCCTGCAAT GTGGTTGAGT GTGATGCTGT
 851 GACAAATCCA GCCAATGGGT TCGTGGAATG TTTCCAAAAC CCTGGAAGCT
 901 TCCCATGGAA CACAACCTGT ACATTTGACT GTGAAGAAGG ATTTGAACTA
 951 ATGGGAGCCC AGAGCCTTCA GTGTACCTCA TCTGGGAATT GGGACAACGA
1001 GAAGCCAACG TGTAAAGCTG TGACATGCAG GGCCGTCCGC CAGCCTCAGA
1051 ATGGCTCTGT GAGGTGCAGC CATTCCCCTG CTGGAGAGTT CACCTTCAAA
1101 TCATCCTGCA ACTTCACCTG TGAGGAAGGC TTCATGTTGC AGGGACCAGC
1151 CCAGGTTGAA TGCACCACTC AAGGGCAGTG GACACAGCAA ATCCAGTTT
1201 GTGAAGCTTT CCAGTGCACA GCCTTGTCCA ACCCCGAGCG AGGCTACATG
1251 AATTGTCTTC CTAGTGCTTC TGGCAGTTTC CGTTATGGGT CCAGCTGTGA
1301 GTTCTCCTGT GAGCAGGGTT TTGTGTTGAA GGGATCCAAA AGGCTCCAAT
1351 GTGGCCCCAC AGGGGAGTGG GACAACGAGA AGCCCACATG TGAAGCTGTG
1401 AGATGCGATG CTGTCCACCA GCCCCCGAAG GGTTTGGTGA GGTGTGCTCA
1451 TTCCCCTATT GGAGAATTCA CCTACAAGTC CTCTTGTGCC TTCAGCTGTG
1501 AGGAGGGATT TGAATTATAT GGATCAACTC AACTTGAGTG CACATCTCAG
1551 GGACAATGGA CAGAAGAGGT TCCTTCCTGC CAAGTGGTAA AATGTTCAAG
1601 CCTGGCAGTT CCGGGAAAGA TCAACATGAG CTGCAGTGGG GAGCCCGTGT
1651 TTGGCACTGT GTGCAAGTTC GCCTGTCCTG AAGGATGGAC GCTCAATGGC
1701 TCTGCAGCTC GGACATGTGG AGCCACAGGA CACTGGTCTG GCCTGCTACC
1751 TACCTGTGAA GCTCCCACTG AGTCCAACAT TCCCTTGGTA GCTGGACTTT
```

-continued
```
1801 CTGCTGCTGG ACTCTCCCTC CTGACATTAG CACCATTTCT CCTCTGGCTT
1851 CGGAAATGCT TACGGAAAGC AAAGAAATTT GTTCCTGCCA GCAGCTGCCA
1901 AAGCCTTGAA TCAGACGGAA GCTACCAAAA GCCTTCTTAC ATCCTTTAAG
1951 TTCAAAAGAA TCAGAAACAG GTGCATCTGG GGAACTAGAG GGATACACTG
2001 AAGTTAACAG AGACAGATAA CTCTCCTCGG GTCTCTGGCC CTTCTTGCCT
2051 ACTATGCCAG ATGCCTTTAT GGCTGAAACC GCAACACCCA TCACCACTTC
2101 AATAGATCAA AGTCCAGCAG GCAAGGACGG CCTTCAACTG AAAAGACTCA
2151 GTGTTCCCTT TCCTACTCTC AGGATCAAGA AAGTGTTGGC TAATGAAGGG
2201 AAAGGATATT TTCTTCCAAG CAAAGGTGAA GAGACCAAGA CTCTGAAATC
2251 TCAGAATTCC TTTTCTAACT CTCCCTTGCT CGCTGTAAAA TCTTGGCACA
2301 GAAACACAAT ATTTTGTGGC TTTCTTTCTT TTGCCCTTCA CAGTGTTTCG
2351 ACAGCTGATT ACACAGTTGC TGTCATAAGA ATGAATAATA ATTATCCAGA
2401 GTTTAGAGGA AAAAAATGAC TAAAAATATT ATAACTTAAA AAAATGACAG
2451 ATGTTGAATG CCCACAGGCA AATGCATGGA GGGTTGTTAA TGGTGCAAAT
2501 CCTACTGAAT GCTCTGTGCG AGGGTTACTA TGCACAATTT AATCACTTTC
2551 ATCCCTATGG GATTCAGTGC TTCTTAAAGA GTTCTTAAGG ATTGTGATAT
2601 TTTTACTTGC ATTGAATATA TTATAATCTT CCATACTTCT TCATTCAATA
2651 CAAGTGTGGT AGGGACTTAA AAAACTTGTA AATGCTGTCA ACTATGATAT
2701 GGTAAAAGTT ACTTATTCTA GATTACCCCC TCATTGTTTA TTAACAAATT
2751 ATGTTACATC TGTTTTAAAT TTATTTCAAA AAGGGAAACT ATTGTCCCCT
2801 AGCAAGGCAT GATGTTAACC AGAATAAAGT TCTGAGTGTT TTTACTACAG
2851 TTGTTTTTTG AAAACATGGT AGAATTGGAG AGTAAAAACT GAATGGAAGG
2901 TTTGTATATT GTCAGATATT TTTTCAGAAA TATGTGGTTT CCACGATGAA
2951 AAACTTCCAT GAGGCCAAAC GTTTTGAACT AATAAAAGCA TAAATGCAAA
3001 CACACAAAGG TATAATTTTA TGAATGTCTT TGTTGGAAAA GAATACAGAA
3051 AGATGGATGT GCTTTGCATT CCTACAAAGA TGTTTGTCAG ATGTGATATG
3101 TAAACATAAT TCTTGTATAT TATGGAAGAT TTTAAATTCA CAATAGAAAC
3151 TCACCATGTA AAAGAGTCAT CTGGTAGATT TTTAACGAAT GAAGATGTCT
3201 AATAGTTATT CCCTATTTGT TTTCTTCTGT ATGTTAGGGT GCTCTGGAAG
3251 AGAGGAATGC CTGTGTGAGC AAGCATTTAT GTTTATTTAT AAGCAGATTT
3301 AACAATTCCA AAGGAATCTC CAGTTTTCAG TTGATCACTG GCAATGAAAA
3351 ATTCTCAGTC AGTAATTGCC AAAGCTGCTC TAGCCTTGAG GAGTGTGAGA
3401 ATCAAAACTC TCCTACACTT CCATTAACTT AGCATGTGTT GAAAAAAAAA
3451 GTTTCAGAGA AGTTCTGGCT GAACACTGGC AACGACAAAG CCAACAGTCA
3501 AAACAGAGAT GTGATAAGGA TCAGAACAGC AGAGGTTCTT TTAAAGGGGC
3551 AGAAAAACTC TGGGAAATAA GAGAGAACAA CTACTGTGAT CAGGCTATGT
3601 ATGGAATACA GTGTTATTTT CTTTGAAATT GTTTAAGTGT TGTAAATATT
3651 TATGTAAACT GCATTAGAAA TTAGCTGTGT GAAATACCAG TGTGGTTTGT
3701 GTTTGAGTTT TATTGAGAAT TTTAAATTAT AACTTAAAAT ATTTTATAAT
3751 TTTTAAAGTA TATATTTATT TAAGCTTATG TCAGACCTAT TTGACATAAC
3801 ACTATAAAGG TTGACAATAA ATGTGCTTAT GTTTAAAAAA AAAAAAAAA
3851 AAAA
```

The nucleotide sequence of the cDNA encoding ELAM-1 is shown below:

```
           ATGA TTGCTTCACA GTTTCTCTCA GCTCTCACTT
151 TGGTGCTTCT CATTAAAGAG AGTGGAGCCT GGTCTTACAA CACCTCCACG
201 GAAGCTATGA CTTATGATGA GGCCAGTGCT TATTGTCAGC AAAGGTACAC
251 ACACCTGGTT GCAATTCAAA ACAAAGAAGA GATTGAGTAC CTAAACTCCA
301 TATTGAGCTA TTCACCAAGT TATTACTGGA TTGGAATCAG AAAAGTCAAC
351 AATGTGTGGG TCTGGGTAGG AACCCAGAAA CCTCTGACAG AAGAAGCCAA
401 GAACTGGGCT CCAGGTGAAC CCAACAATAG GCAAAAAGAT GAGGACTGCG
451 TGGAGATCTA CATCAAGAGA GAAAAAGATG TGGGCATGTG GAATGATGAG
501 AGGTGCAGCA AGAAGAAGCT TGCCCTATGC TACACAGCTG CCTGTACCAA
551 TACATCCTGC AGTGGCCACG GTGAATGTGT AGAGACCATC AATAATTACA
601 CTTGCAAGTG TGACCCTGGC TTCAGTGGAC TCAAGTGTGA GCAAATTGTG
651 AACTGTACAG CCCTGGAATC CCCTGAGCAT GGAAGCCTGG TTTGCAGTCA
701 CCCACTGGGA AACTTCAGCT ACAATTCTTC CTGCTCTATC AGCTGTGATA
751 GGGGTTACCT GCCAAGCAGC ATGGAGACCA TGCAGTGTAT GTCCTCTGGA
801 GAATGGAGTG CTCCTATTCC AGCCTGCAAT GTGGTTGAGT GTGATGCTGT
851 GACAAATCCA GCCAATGGGT TCGTGGAATG TTTCCAAAAC CCTGGAAGCT
901 TCCCATGGAA CACAACCTGT ACATTTGACT GTGAAGAAGG ATTTGAACTA
951 ATGGGAGCCC AGAGCCTTCA GTGTACCTCA TCTGGGAATT GGGACAACGA
```

-continued

```
1001 GAAGCCAACG TGTAAAGCTG TGACATGCAG GGCCGTCCGC CAGCCTCAGA

1051 ATGGCTCTGT GAGGTGCAGC CATTCCCCTG CTGGAGAGTT CACCTTCAAA

1101 TCATCCTGCA ACTTCACCTG TGAGGAAGGC TTCATGTTGC AGGGACCAGC

1151 CCAGGTTGAA TGCACCACTC AAGGGCAGTG GACACAGCAA ATCCCAGTTT

1201 GTGAAGCTTT CCAGTGCACA GCCTTGTCCA ACCCCGAGCG AGGCTACATG

1251 AATTGTCTTC CTAGTGCTTC TGGCAGTTTC CGTTATGGGT CCAGCTGTGA

1301 GTTCTCCTGT GAGCAGGGTT TTGTGTTGAA GGGATCCAAA AGGCTCCAAT

1351 GTGGCCCCAC AGGGGAGTGG GACAACGAGA AGCCCACATG TGAAGCTGTG

1401 AGATGCGATG CTGTCCACCA GCCCCCGAAG GGTTTGGTGA GGTGTGCTCA

1451 TTCCCCTATT GGAGAATTCA CCTACAAGTC CTCTTGTGCC TTCAGCTGTG

1501 AGGAGGGATT TGAATTATAT GGATCAACTC AACTTGAGTG CACATCTCAG

1551 GGACAATGGA CAGAAGAGGT TCCTTCCTGC CAAGTGGTAA AATGTTCAAG

1601 CCTGGCAGTT CCGGGAAAGA TCAACATGAG CTGCAGTGGG GAGCCCGTGT

1651 TTGGCACTGT GTGCAAGTTC GCCTGTCCTG AAGGATGGAC GCTCAATGGC

1701 TCTGCAGCTC GGACATGTGG AGCCACAGGA CACTGGTCTG GCCTGCTACC

1751 TACCTGTGAA GCTCCCACTG AGTCCAACAT TCCCTTGGTA GCTGGACTTT

1801 CTGCTGCTGG ACTCTCCCTC CTGACATTAG CACCATTTCT CCTCTGGCTT

1851 CGGAAATGCT TACGGAAAGC AAAGAAATTT GTTCCTGCCA GCAGCTGCCA

1901 AAGCCTTGAA TCAGACGGAA GCTACCAAAA GCCTTCTTAC ATCCTTTAA
```

The translated amino acid sequence of ELAM-1 is shown below:

```
                                        M I
A S Q F L S A L T L V L L I K E S G A W
S Y N T S T E A M T Y D E A S A Y C Q Q
R Y T H L V A I Q N K E E I E Y L N S I
L S Y S P S Y Y W I G I R K V N N V W V
W V G T Q K P L T E E A K N W A P G E P
N N R Q K D E D C V E I Y I K R E K D V
G M W N D E R C S K K K L A L C Y T A A
C T N T S C S G H G E C V E T I N N Y T
C K C D P G F S G L K C E Q I V N C T A
L E S P E H G S L V C S H P L G N F S Y
N S S C S I S C D R G Y L P S S M E T M
Q C M S S G E W S A P I P A C N V V E C
D A V T N P A N G F V E C F Q N P G S F
P W N T T C T F D C E E G F E L M G A Q
S L Q C T S S G N W D N E K P T C K A V
T C R A V R Q P Q N G S V R C S H S P A
G E F T F K S S C N F T C E E G F M L Q
G P A Q V E C T T Q G Q W T Q Q I P V C
E A F Q C T A L S N P E R G Y M N C L P
S A S G S F R Y G S S C E F S C E Q G F
V L K G S K R L Q C G P T G E W D N E K
P T C E A V R C D A V H Q P P K G L V R
C A H S P I G E F T Y K S S C A F S C E
E G F E L Y G S T Q L E C T S Q G Q W T
E E V P S C Q V V K C S S L A V P G K I
N M S C S G E P V F G T V C K F A C P E
G W T L N G S A A R T C G A T G H W S G
L L P T C E A P T E S N I P L V A G L S
A A G L S L L T L A P F L L W L R K C L
R K A K K F V P A S S C Q S L E S D G S
Y Q K P S Y I L
```

The translated amino acid sequence of pELAM-1 suggests typical features of a transmembrane protein. For example, the extracellular domain contains eleven potential N-linked glycosylation sites.

Example 3

Functional Studies

Mab 18/7 inhibits the adhesion of PMN (>50%) and HL-60 cells (>60%) to activated HEC monolayers. Bevilacqua, M. P., et al., Proc. Natl. Acad. Sci., USA 84:9238-9242 (1987). From these studies, it appeared that ELAM-1 may promote leukocyte adhesion by acting as a ligand for a leukocyte cell surface receptor. This hypothesis is further supported by the present studies using cloned ELAM-1. Transfection of COS cells with pELAM-1 promotes the adhesion of HL-60 cells. Immunoperoxidase staining revealed a direct correlation between COS cell expression of ELAM-1 and HL-60 cell adhesion. Mab H18/7 was found to abate (100±3% inhibition, mean ±SEM, 3 exp.), the augmented adhesion to pELAM transfected COS cells.

Example 4

Expression of Natural ELAM-1

Figure 2:
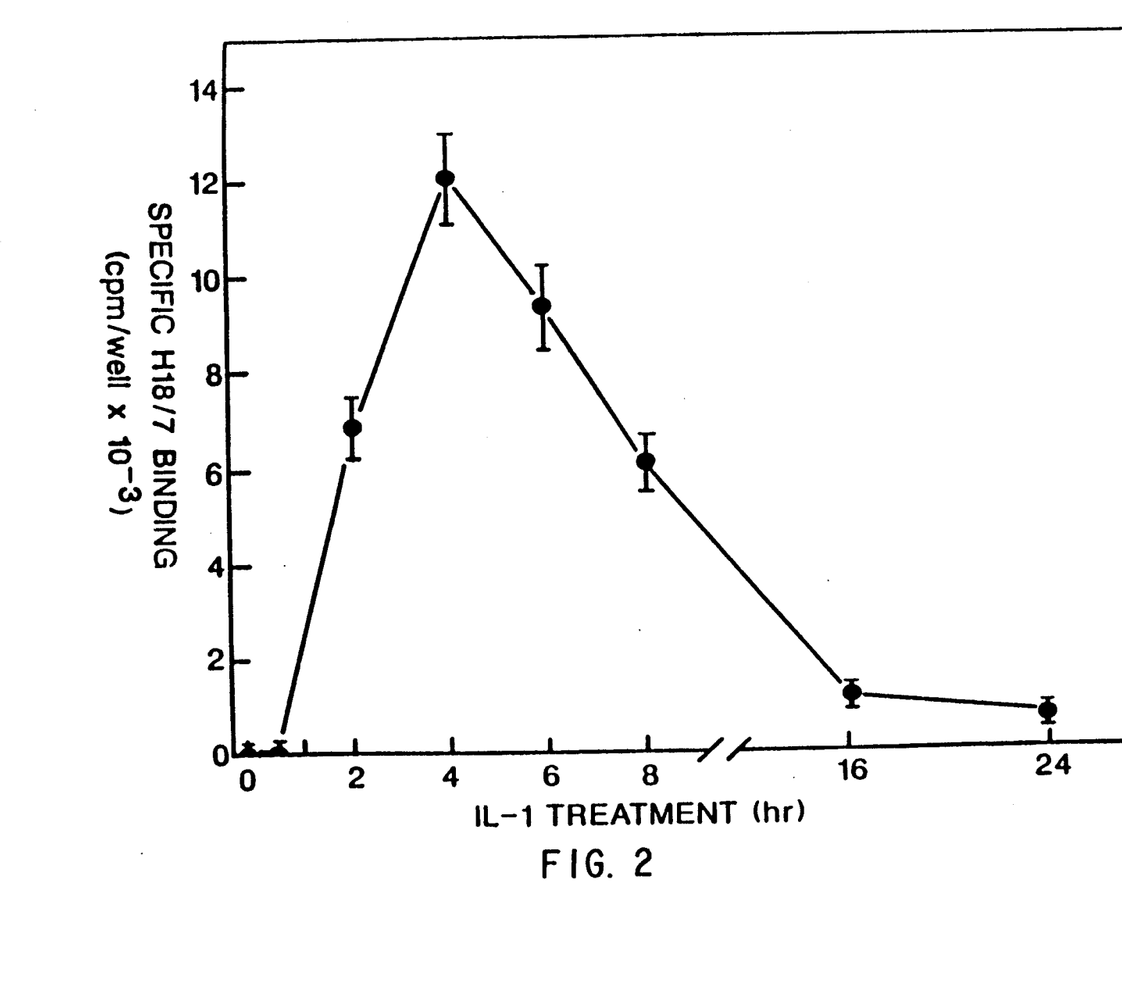
FIG. 2 depicts a graph showing the specific binding of H18/7 to HEC monolayers for various times after treatment with IL-1.

Previous studies have demonstrated that unstimulated HEC express little or no ELAM-1. Bevilacqua, M. P., et al., Proc. Natl. Acad. Sci. (USA) 84:9238-9242 (1987). Treatment of HEC monolayers for 4 hr with rIL-1 (5 U/ml) or rTNF (200 U/ml) resulted in the production of anti-ELAM-1 precipitable species. Similar results were obtained with lymphotoxin (200 U/ml) and bacterial endotoxin (10 ug/ml). No induction of ELAM-1 was observed after treatment of the HEC with IFN (200 U/ml). RNA blot analysis showed a primary species of 3.9 kb in HEC treated for 2 hr with rIL-1 or rTNF, that was absent in unstimulated and IFN-stimulated HEC. Continuous exposure of HEC monolayers to rIL-1 results in a rapid increase in the expression of ELAM-1 with onset at 1–2 hr, and peak at 4–6 hr, followed by a decline toward basal levels by 24 hrs. As shown in FIG. 2, endothelial cell surface expression of ELAM-1, as detected in an immunobinding assay, correlates temporally with the expression of ELAM-1 mRNA. Thus, endothelial cell expression of ELAM-1 can be induced by several mediators including rIL-1 and rTNF. These effects are time-dependent and appear to occur, at least in part, at a transcriptional level. Blot hybridization of genomic DNA from placenta revealed a pattern consistent with a single-copy gene.

CONCLUSIONS

ELAM-1 is a novel cell surface glycoprotein with sequence homologies to a variety of complement binding proteins including complement receptor 1 (CR1), complement receptor 2 (CR2), complement Factor H and C4 binding protein as well as some complement-binding proteins such as $\beta_2$-glycoprotein I. These homologies suggest the existence of a family of related proteins. The translated amino acid sequences of ELAM-1 reveal typical features of a transmembrane protein including a leader sequence. The extracellular domain contains eleven potential N-linked glycosylation sites and studies with endoglycosidase H suggest that N-linked carbohydrates account for about 40% of the total molecular mass (Mr 115,000) of mature endothelial ELAM-1. In addition, these studies, in conjunction with pulse-chase labeling procedures, provide strong evidence that the two polypeptides immunoprecipitated from activated HEC by anti-ELAM-1 Mabs are composed of the same polypeptide backbone; the difference in molecular mass between the two species appears to involve post-translational modification, probably at the level of carbohydrate processing.

The inducible expression of ELAM-1 may be of central importance in its role in leukocyte-vessel wall interactions. The data indicates that certain inflammatory/immune cytokines including IL-1 and TNF, but not IFN-, act on endothelial cells to induce the biosynthesis and expression of ELAM-1. RNA blot analysis suggests that the induction of ELAM-1 occurs, in large part, at the transcriptional level. Previous studies with Mab H4/18 have demonstrated focal endothelial expression of ELAM-1 in a variety of pathophysiological settings.

Having now fully described this invention, it will be understood by those of skill in the art that the same can be performed within a wide and equivalent range of conditions, formulations, and other parameters without affecting the scope of the invention or any embodiment thereof.

What is claimed is:

1. A cloned gene obtained by the recombinant DNA technology encoding ELAM-1 and having the following amino acid sequence:

```
                                      M I
A S Q F L S A L T L V L L I K E S G A W
S Y N T S T E A M T Y D E A S A Y C Q Q
R Y T H L V A I Q N K E E I E Y L N S I
L S Y S P S Y Y W I G I R K V N N V W V
W V G T Q K P L T E E A K N W A P G E P
N N R Q K D E D C V E I Y I K R E K D V
G M W N D E R C S K K K L A L C Y T A A
C T N T S C S G H G E C V E T I N N Y T
C K C D P G F S G L K C E Q I V N C T A
L E S P E H G S L V C S H P L G N F S Y
N S S C S I S C D R G Y L P S S M E T M
Q C M S S G E W S A P I P A C N V V E C
D A V T N P A N G F V E C F Q N P G S F
P W N T T C T F D C E E G F E L M G A Q
S L Q C T S S G N W D N E K P T C K A V
T C R A V R Q P Q N G S V R C S H S P A
G E F T F K S S C N F T C E E G F M L Q
G P A Q V E C T T Q G Q W T Q Q I P V C
E A F Q C T A L S N P E R G Y M N C L P
S A S G S F R Y G S S C E F S C E Q G F
V L K G S K R L Q C G P T G E W D N E K
P T C E A V R C D A V H Q P P K G L V R
C A H S P I G E F T Y K S S C A F S C E
E G F E L Y G S T Q L E C T S Q G Q W T
E E V P S C Q V V K C S S L A V P G K I
N M S C S G E P V F G T V C K F A C P E
G W T L N G S A A R T C G A T G H W S G
L L P T C E A P T E S N I P L V A G L S
A A G L S L L T L A P F L L W L R K C L
R K A K K F V P A S S C Q S L E S D G S
Y Q K P S Y I L.
```

2. A vector comprising the cloned gene of claim 1.

3. A bacterial or mammalian cell line transformed with the vector of claim 2.

* * * * *

UNITED STATES PATENT AND TRADEMARK OFFICE
CERTIFICATE OF CORRECTION

PATENT NO. : 5,081,034
DATED : January 14, 1992
INVENTOR(S) : Bevilacqua et al

It is certified that error appears in the above-identified patent and that said Letters Patent is hereby corrected as shown below:

Column 1, delete the paragraph immediately after the heading "STATEMENT AS TO RIGHTS TO INVENTIONS MADE UNDER FEDERALLY SPONSORED RESEARCH AND DEVELOPMENT" and insert the following in place thereof:

--This invention was made with government support under PO1 HL 36028/22602 and T32HL 07066 awarded by the National Institutes of Health. The government has certain rights in the invention.--

Signed and Sealed this

Twenty-eighth Day of June, 1994

Attest:

BRUCE LEHMAN

Attesting Officer     Commissioner of Patents and Trademarks

UNITED STATES PATENT AND TRADEMARK OFFICE
CERTIFICATE OF CORRECTION

PATENT NO. : 5,081,034
DATED : January 14, 1992
INVENTOR(S) : Michael P. Bevilacqua et al It is certified that error appears in the above-indentified patent and that said Letters Patent is hereby corrected as shown below:

On the title page: Item [73] under the heading "Assignee," immediately after "Brigham & Women's Hospital, Boston, Mass.," insert:

--; General Hospital Corporation, Boston, Mass.--

Signed and Sealed this

Fourteenth Day of March, 1995

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,081,034
DATED : JANUARY 14, 1992
INVENTOR(S) : Bevilacqua et al

It is certified that error appears in the above-indentified patent and that said Letters Patent is hereby corrected as shown below:

On the title page: Item[73], under the heading "Assignee" before "General Hospital Corporation, "insert --The--.

This certificate supercedes Certificate of Correction issued March 14, 1995.

Signed and Sealed this

Thirtieth Day of April, 1996

Attest:

BRUCE LEHMAN

Attesting Officer   Commissioner of Patents and Trademarks